United States Patent [19]

Raynolds

[11] 4,366,329

[45] Dec. 28, 1982

[54] PROCESS FOR THE SEPARATION OF META AND PARA ISOMERS OF THE SODIUM SALT OF BROMOPHENOL

[75] Inventor: Peter W. Raynolds, Kingsport, Tenn.

[73] Assignee: Eastman Kodak Company, Rochester, N.Y.

[21] Appl. No.: 276,271

[22] Filed: Jun. 22, 1981

[51] Int. Cl.$^3$ ....................... C07C 39/27; C07C 37/68
[52] U.S. Cl. .................................. 568/755; 568/751; 568/774
[58] Field of Search ............... 568/750, 751, 755, 749, 568/774, 778, 725, 777, 776

[56] References Cited

U.S. PATENT DOCUMENTS

| | | | |
|---|---|---|---|
| 2,319,960 | 12/1943 | Traecy ................................. | 568/774 |
| 2,452,154 | 10/1948 | Ross .................................... | 568/779 |
| 3,014,079 | 12/1961 | Olin ..................................... | 568/755 |
| 3,159,685 | 12/1964 | Bradley et al. ...................... | 568/755 |
| 3,293,309 | 9/1966 | Zemba ................................. | 568/774 |
| 3,412,145 | 11/1968 | Hanna ................................. | 568/778 |
| 3,462,498 | 8/1969 | Lowe .................................. | 568/755 |
| 3,471,577 | 10/1969 | Hauebin ............................. | 568/778 |
| 3,499,045 | 3/1970 | Cleary ................................ | 568/755 |
| 3,772,394 | 11/1973 | Milnes ................................ | 568/751 |
| 3,912,782 | 10/1975 | Kiel .................................... | 568/774 |

FOREIGN PATENT DOCUMENTS

| | | | |
|---|---|---|---|
| 1316276 | 5/1973 | United Kingdom ................ | 568/774 |
| 401659 | 3/1974 | U.S.S.R. ............................. | 568/755 |

OTHER PUBLICATIONS

Fury et al., "J. Organic Chemistry", vol. 30, pp. 2301–2304, (1965).

*Primary Examiner*—Werren B. Lone
*Attorney, Agent, or Firm*—Gary C. Bailey; J. Frederick Thomsen; Daniel B. Reece, III

[57] ABSTRACT

Disclosed is a novel process for the separation of meta and para isomers of the sodium salt of bromophenol. Derivatives of the sodium salt of metabromophenol are useful chemical intermediates.

2 Claims, No Drawings

PROCESS FOR THE SEPARATION OF META AND PARA ISOMERS OF THE SODIUM SALT OF BROMOPHENOL

This invention concerns a novel process for separating meta and para isomers of the sodium salt of bromophenol.

Derivatives of the sodium salt of meta-bromophenol such as the free phenol and alkyl ethers thereof are useful chemical intermediates. Up until now obtaining such compounds in a high degree of purity has been difficult since bromination of phenol gives a monobrominated phenol consisting primarily of p-bromophenol. Fury et al, J. Org. Chem., 30, 2301 (1965), disclose a means for converting para-bromophenol to a mixture consisting of 54% meta and 46% para-bromophenol. However, obtaining the meta-isomer substantially free of the para-isomer still posed a problem. The close boiling ranges of the meta and para isomers (236° C. and 238° C. respectively) precludes separation of the isomer mixture by fractional distillation. Alternate reaction processes for preparation of the meta isomer require lengthy, multistep processes.

For most substituted phenolate compounds, the meta-isomer is substantially more water-soluble than is the para-isomer. For example, U.S. Pat. No. 3,014,079 discloses the separation of meta and para alkylphenols by dissolving a mixture of the isomers in dilute aqueous sodium hydroxide and subsequently adding additional alkali to selectively precipitate the sodium salt of the para alkyl phenol.

I have discovered that sodium m-bromophenolate can be selectively precipitated from an aqueous solution of a mixture of sodium m-bromophenolate and para-bromophenolate. The meta isomer product initially obtained normally contains not more than 10 weight percent of the para isomer. If desired, the product may be purified further by repeating the dissolution and precipitation procedure, and thereby reduce the para isomer content to not more than 2 weight percent.

Both the preparation of the aqueous solution of the mixture of sodium para and meta bromophenolates and the means by which the meta isomer is precipitated are carried out by conventional methods and thus are not a part of this invention. For example, the solution may be prepared according to the procedure employed in U.S. Pat. No. 3,014,079. That procedure may be modified by including initially sufficient sodium hydroxide to effect, i.e., salt out, the meta isomer when the solution is cooled. By simple filtration the meta isomer is thus easily separated from the unwanted para isomer which remains in the filtrate.

My process is not limited to the isomeric proportions disclosed in Fury et al, and is equally effective with isomeric mixtures of higher or lower concentrations of the para isomer. Generally, an aqueous solution containing about 20 to 50% sodium hydroxide may be employed in the reaction process while the mole concentration of sodium hydroxide to the isomeric mixture of meta and para bromophenol will normally be in the range of about 1–20:1, with about 11:1 being preferred. The reaction process is conveniently carried out at room temperature. Upon completion of the reaction, the reaction mixture may be cooled by water bath to room temperature (25° C.) to enhance precipitation of the meta isomer product. If desired, the meta isomer can be isolated in equal yields by acidification of the sodium salt.

My novel process will be further illustrated by the following example:

EXAMPLE

A mixture consisting of 53% of meta bromophenol and 47% of para bromophenol (30.15 g, 0.174 mol) was dissolved in 150 ml of 50% sodium hydroxide and 30 ml of water and cooled to 25° C., whereupon a white solid precipitated. The white solid was filtered and slurried with 20 ml of 50% sodium hydroxide and 5 ml of water. The white solid was then crystallized again in a similar manner and methylated with an excess of dimethylsulfate and sodium hydroxide to yield 9.72 g (30%) of meta bromoanisole after distillation, containing less than 2% of the para isomer.

The invention has been described in detail with particular reference to certain preferred embodiments thereof, but it will be understood that variations and modifications can be effected within the spirit and scope of the invention.

I claim:

1. Process for separating meta and para isomers of a sodium salt of bromophenol which comprises adding sodium hydroxide to an aqueous solution of a mixture of meta and para bromophenol to precipitate the meta isomer.

2. Process for separating meta and para isomers of a sodium salt of bromophenol which comprises adding sodium hydroxide to an aqueous solution of a mixture of meta and para bromophenol to precipitate the meta isomer wherein the mole ratio of sodium hydroxide to the meta and para isomer mixture is 11:1.

* * * * *